United States Patent
Hastings

(10) Patent No.: US 6,873,915 B2
(45) Date of Patent: Mar. 29, 2005

(54) PEAK SELECTION IN MULTIDIMENSIONAL DATA

(75) Inventor: Curtis A. Hastings, San Francisco, CA (US)

(73) Assignee: Surromed, Inc., Menlo Park, CA (US)

( * ) Notice: Subject to any disclaimer, the term of this patent is extended or adjusted under 35 U.S.C. 154(b) by 61 days.

(21) Appl. No.: 10/226,090

(22) Filed: Aug. 22, 2002

(65) Prior Publication Data

US 2003/0040123 A1 Feb. 27, 2003

Related U.S. Application Data

(60) Provisional application No. 60/314,841, filed on Aug. 24, 2001.

(51) Int. Cl.[7] .............................................. G06F 19/00
(52) U.S. Cl. ........................... 702/22; 702/30; 702/27; 702/32; 250/282
(58) Field of Search ........................ 702/22, 23, 27, 702/28, 30–32, 66, 69, 71, 70, 73, 78, 179, 180, 189, 191, 193, 195, 181; 250/281, 282, 339.07, 339.12; 73/23.22, 23.35–23.37; 436/171, 173; 422/89

(56) References Cited

U.S. PATENT DOCUMENTS

| | | | |
|---|---|---|---|
| 3,997,298 A | 12/1976 | McLafferty et al. | 422/70 |
| 4,752,888 A | 6/1988 | Yoshihara | 702/32 |
| 5,119,315 A | 6/1992 | Kemp et al. | 702/27 |
| 5,592,402 A | 1/1997 | Beebe et al. | 703/6 |
| 5,672,869 A | 9/1997 | Windig et al. | 250/282 |
| 5,885,841 A | 3/1999 | Higgs, Jr. et al. | 436/89 |
| 5,995,989 A | 11/1999 | Gedcke et al. | 708/300 |
| 6,008,490 A * | 12/1999 | Kato | 250/282 |
| 6,008,896 A | 12/1999 | Sabsabi et al. | 356/318 |
| 6,091,492 A | 7/2000 | Strickland et al. | 356/336 |
| 6,112,161 A | 8/2000 | Dryden et al. | 702/85 |
| 6,147,344 A * | 11/2000 | Annis et al. | 250/281 |
| 6,207,955 B1 | 3/2001 | Wells et al. | 250/288 |
| 6,253,162 B1 * | 6/2001 | Jarman et al. | 702/179 |
| 6,278,794 B1 | 8/2001 | Parekh et al. | 382/129 |
| 6,391,649 B1 | 5/2002 | Chait et al. | 436/173 |
| 6,421,612 B1 | 7/2002 | Agrafiotis et al. | 702/19 |
| 6,449,584 B1 * | 9/2002 | Bertrand et al. | 702/180 |
| 6,526,299 B2 | 2/2003 | Pickard | 600/310 |
| 6,642,059 B2 | 11/2003 | Chait et al. | 436/173 |
| 6,753,966 B2 | 6/2004 | Von Rosenberg | 356/432 |
| 2001/0019829 A1 | 9/2001 | Nelson et al. | 435/7.1 |
| 2002/0102610 A1 | 8/2002 | Townsend et al. | 435/7.1 |

FOREIGN PATENT DOCUMENTS

| | | |
|---|---|---|
| WO | WO 98/1661 | 4/1998 |
| WO | WO 00/67017 | 11/2000 |
| WO | WO 01/35266 | 5/2001 |

OTHER PUBLICATIONS

Gygi et al. (1999) Nat. Biotech. 17:994–999, no month.
do Lago et al. (1995) Anal. Chim. Acta, 310: 281–288, no month.

(Continued)

*Primary Examiner*—Hal Wachsman
(74) *Attorney, Agent, or Firm*—Swanson & Bratschun, LLC

(57) ABSTRACT

An automatic peak selection method for multidimensional data that selects peaks from very noisy data such as two-dimensional liquid chromatography-mass spectrometry (LC-MS) data is described. Such data are characterized by non-normally distributed noise that varies in different dimensions. The method computes local noise thresholds for each one-dimensional component of the data. Each point has a local noise threshold applied to it for each dimension of the data set, and a point is selected as a candidate peak only if its value exceeds all of the applied local noise thresholds. Contiguous candidate peaks are clustered into actual peaks. The method is preferably implemented as part of a high-throughput platform for analyzing complex biological mixtures.

17 Claims, 7 Drawing Sheets

OTHER PUBLICATIONS

Windig et al. (1996) Anal. Chem., 68: 3602–3606, no month.
Schoonjans et al. (2000) J. Pharm. & Biomed. Analysis 21:1197–1214, no month.
Fiehn et al. (2000) Nat. Biotech. 18:1157–1161.
Chelius et al. (2002) J. Proteome Res. 1:317–323, no month.
Bryant et al. (2001) Rapid Commun. Mass Spectrom. 15:418–427, no month.
Wang et al. (1987) Analytical Chemistry 59:649–654, no month.
Aach & Church (2001) Bioinformatics 17:495–508, no month.
Nielsen et al. (1998) J. of Chromatography A. 805:17–35, no month.
Bylund et al. (2002) J. of Chromatography A. 961:237–244, no month.
Pravdova et al. (2002) Analytica Chimica Acta 456:77–92, no month.
Kassidas et al. (1998) AIChE Journal 44(4):864–875, no month.
Grung & Kvalheim (1995) Analytica Chimica Acta 304:57–66, no month.
Prazen et al. (Jan. 15, 1998) Anal. Chem. 70:218–225, no month.
Sakoe & Chiba (2002) IEEE Transactions on Acoustics, Speech and Signal Processing ASSP26(1):43–49.
Breen et al. (2000) Electrophoresis 21:2243–2251, no month.
Koradi et al. (1998) *J. Magn. Reson.*, 135:288–297, no month.
Stein (1999) J Am Soc Mass Spectrum 10:770–781, no month.
Hastings et al. (2002) Rapid Communications in Mass Spectrometry 16(5):462–465,467.(No month).

* cited by examiner

PEAK SELECTION IN MULTIDIMENSIONAL DATA

CROSS-REFERENCE TO RELATED APPLICATIONS

This application claims the benefit of U.S. Provisional Application No. 60/314,841, "Peak Selection in Multidimensional Data," filed Aug. 24, 2001, incorporated herein by reference.

FIELD OF THE INVENTION

This invention relates generally to analysis of data collected by analytical techniques such as chromatography and spectrometry. More particularly, it relates to a peak detection method for multidimensional data such as liquid chromatography-mass spectrometry (LC-MS) data.

BACKGROUND OF THE INVENTION

Liquid chromatography-mass spectrometry (LC-MS) is a well-known combined analytical technique for separation and identification of chemical mixtures. Components of a mixture pass through a chromatographic column at different rates, and the eluent is subjected to mass spectrometric analysis at known time intervals. Data are acquired as a series of time-dependent mass spectra, i.e., ion intensity at varying mass-to-charge ratios (m/z).

LC-MS data are typically reported by the mass spectrometer as a total ion current (TIC) chromatogram, the sum of all detected ions at each scan time. A TIC chromatogram of a proteolytic digest of human serum is shown in FIG. 1, with peaks representing separated components of the mixture eluting at the indicated retention times. Mass spectra corresponding to identified chromatographic peaks can provide chemical structure information about the peak constituents.

LC-MS has been used traditionally to study relatively simple samples, characterized by large available volumes and small numbers of samples and mixture components, leading to spectra containing few peaks. Recently, the method has been applied to proteomic and metabolomic profiling of complex biological mixtures. In such studies, many samples, each containing a large number of components, are analyzed rapidly, and large amounts of data are collected for mining and statistical analysis. While mass spectra acquired in traditional experimental studies can be interpreted manually, high-throughput studies require automated selection of peaks. Because spectra of complex biological samples tend to contain a large number of overlapping peaks and be very noisy, accurate automatic peak picking is a difficult problem to address.

State-of-the-art LC-MS instruments provide a basic peak picking function for both chromatograms and mass spectra. A noise threshold level is determined automatically, and local maxima in clusters of points above the threshold are identified as peaks. The operator can instead specify a threshold above which the system designates local maxima as peaks. In other methods, the base peak, i.e., the highest peak in the chromatogram, is identified, and all points whose intensities exceed a preset fraction of the base peak are identified as peaks. In practice, however, although the peak picking is performed automatically, it is not intended to be fully automated, but rather to serve as an aid to the operator in analyzing and interpreting the data. Note also that LC-MS data is two-dimensional; that is, a discrete data point (intensity) is obtained for varying values of two independent variables, retention time and mass-to-charge ratio (m/z). Commercially available peak picking methods are applied to one-dimensional data only, i.e., individual mass spectra or chromatograms. For example, Waters's MASSLYNX™ and Thermo Finnigan's XCALIBUR™ are LC-MS software packages that have a peak selection feature. FIG. 2 is an unprocessed base peak trace of the TIC chromatogram of FIG. 1 showing peaks selected by XCALIBUR™ LC-MS software package. The peak selection features of both software packages, however, appear to locate peaks along the time axis only.

A method for filtering and recognizing peaks in spectrometry data is disclosed in U.S. Pat. No. 5,995,989, issued to Gedcke et al. An average background signal level and an average deviation from the background are computed and used to define a local threshold value for each point. Points exceeding the threshold are assumed to be peaks or near peaks. This method was developed for mass spectra, and therefore provides a one-dimensional peak recognition algorithm only. Although it can be applied to two- and higher-dimensional data such as two-dimensional LC-MS data, e.g., by selecting peaks in each mass spectrum and then combining the resulting mass spectra into a total ion current chromatogram, the method's analysis remains one-dimensional. Such a method is limited because it does not take advantage of the information provided by the chromatography dimension. That is, what appears to be a peak in a single mass spectrum may be below the noise threshold in a corresponding mass chromatogram (ion abundance versus retention time for a particular m/z value).

More extensive and multidimensional peak picking algorithms have been developed for nuclear magnetic resonance (NMR) spectroscopy, in which manual peak selection is more time consuming and therefore provides a greater incentive for automation. For example, an automated peak picking algorithm for multidimensional NMR spectra is disclosed in R. Koradi et al., "Automated Peak Picking and Peak Integration in Macromolecular NMR Spectra Using AUTOPSY," *J. Magn. Reson.*, 13: 288–297 (1998). In one feature of the AUTOPSY (automated peak picking for NMR spectroscopy) algorithm, a different local noise level is defined for each multi-dimensional data point, and the point is retained only if its value exceeds the local noise level. A given point's local noise level is a function of the average noise level for all one-dimensional slices passing through the point.

Existing multidimensional peak picking algorithms, such as AUTOPSY, are generally not sufficiently effective at selecting peaks in LC-MS data to allow fully automated peak detection. Moreover, various aspects of LC-MS data render it not amenable to such analysis. For example, LC-MS noise arises from a variety of unrelated and, in some cases, poorly understood sources, and is therefore difficult to filter effectively using methods developed for noise with well-known distributions, such as those found in NMR data. In addition, it is not uncommon for one mass-to-charge ratio to be very noisy, while a single retention time shows little noise. Using the AUTOPSY algorithm, however, a point at the intersection of the noisy mass and low-noise retention time has a threshold level determined equally by the noise level within each one-dimensional slice. Such a level may be too low to exclude all of the noise. This algorithm and other available methods are therefore not optimal for peak peaking in LC-MS data.

There is still a need, therefore, for an automated peak picking algorithm for LC-MS and other multidimensional data.

SUMMARY OF THE INVENTION

The present invention provides a method for automatic peak selection in multidimensional data. Each point of an n-dimensional data set has up to n different one-dimensional peak selection criteria applied to it, and a point can be selected as a peak only if it satisfies all (or some threshold number) of the applied one-dimensional criteria. The method is effective at selecting peaks in very noisy multi-dimensional data, as well as in data having non-normally distributed noise or noise levels that differ dramatically in different dimensions. As a result, the method facilitates automation of high-throughput analysis of small volumes of biological fluids by two-dimensional analytical techniques such as liquid chromatography-mass spectrometry.

In one embodiment, the invention provides a method for automatically detecting peaks in an n-dimensional data set by independently applying m one-dimensional selection criteria to each point in the data set, where $2 \leq m \leq n$. Next, candidate peaks are identified in the points, i.e., those points that satisfy p of the selection criteria applied to them, where $2 \leq p \leq m$. Preferably, candidate peaks satisfy m or n applied selection criteria. Each one-dimensional selection criterion applied to a point corresponds to one of the n dimensions of the data set. Preferably, the selection criteria are noise thresholds, and a point whose value exceeds a noise threshold satisfies the criterion. Noise thresholds are computed from a subset of the data points, and preferably from a median of points in the subset. A particular point's criteria are preferably specific to the point, i.e., locally computed from the n (or fewer) one-dimensional components of the data set that contain the point. Thus each dimension has multiple corresponding selection criteria, and different data points may have different criteria applied to them.

After candidate peaks have been selected, a peak recognition algorithm is applied to select actual peaks from the candidate peaks. Preferably, peaks are clusters of contiguous candidate peaks, because peaks generally have an associated width, but additional peak recognition algorithms, such as lineshape analysis or Bayesian/Maximum Likelihood analysis (for mass chromatograms) or isotope distribution analysis (for mass spectra), can also be applied.

The present invention also provides a method for detecting components in a chemical mixture, by subjecting the mixture to chromatography and mass spectrometry using an instrument, acquiring a two-dimensional data set from the instrument, and analyzing the acquired data to identify candidate peaks. The data consist of mass spectra and mass chromatograms, and local noise thresholds are computed for each spectrum and chromatogram. Both corresponding thresholds are applied to each point, and candidate peaks are identified as points exceeding both thresholds. Noise thresholds are preferably computed from a median of the nonzero points in the chromatogram or spectrum.

Also provided by the present invention is a program storage device accessible by a processor, tangibly embodying a program of instructions executable by the processor to perform method steps for an automatic peak detection method as described above.

DETAILED DESCRIPTION OF THE INVENTION

Figure 1:
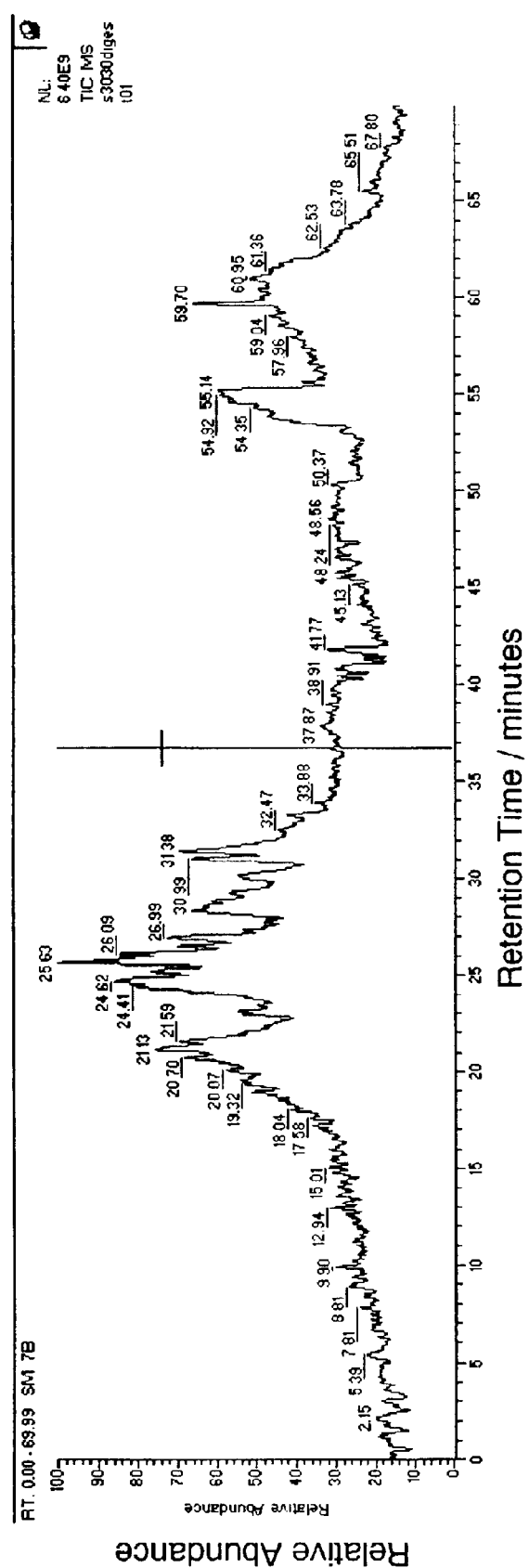
FIG. 1 is a total ion current (TIC) chromatogram of a proteolytic digest of human serum analyzed by liquid chromatography-mass spectrometry (LCMS), as known in the prior art.
Figure 2:
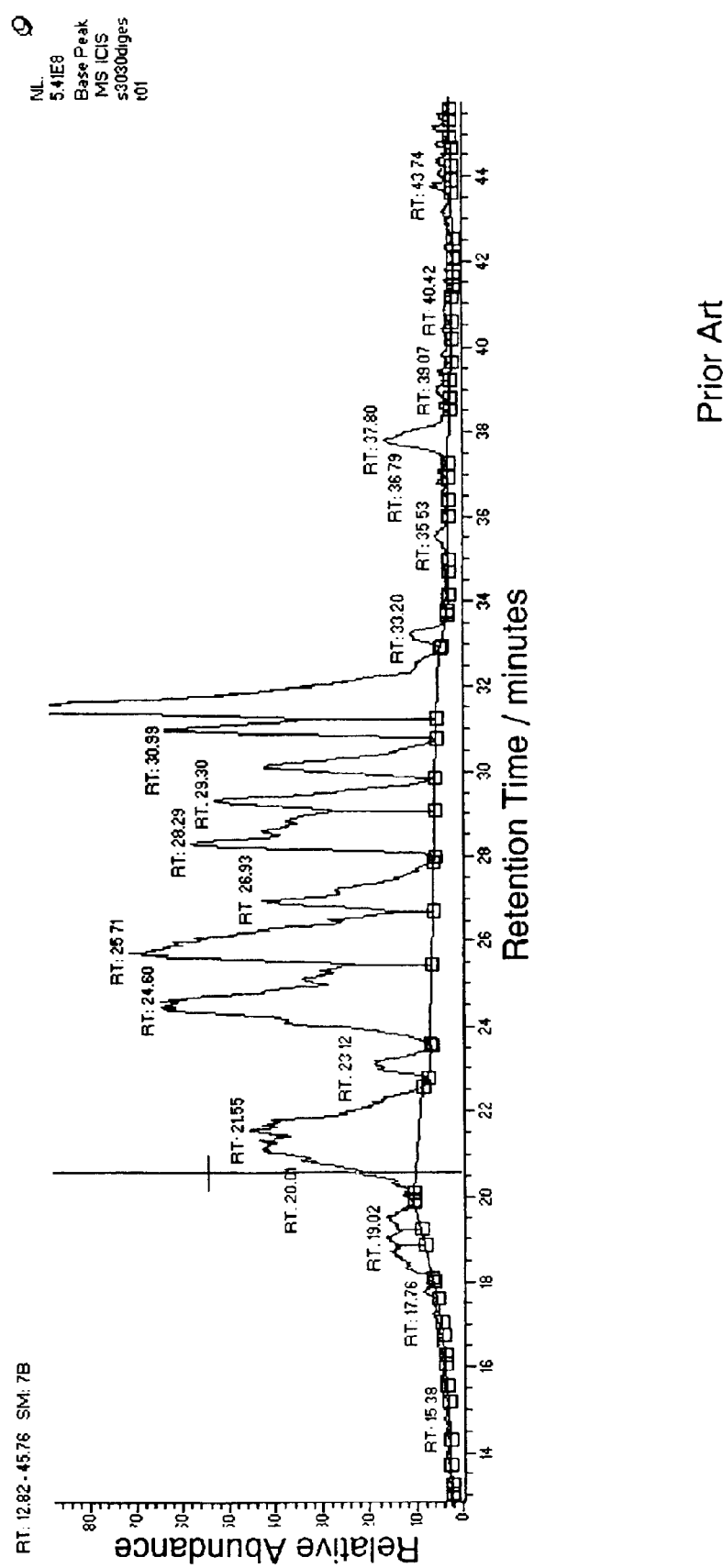
FIG. 2 is a prior art base peak trace of the chromatogram of FIG. 1, with peaks selected according to a prior art algorithm (ThermoFinnigan XCALIBUR™ LC-MS software package).

The present invention provides a method for automatic peak selection in multidimensional data. For illustration purposes, the invention will be described with respect to two-dimensional liquid chromatography-mass spectrometry (LC-MS) data. However, it is to be understood that the invention can be applied to any type of multidimensional data (i.e., two or more dimensions). The invention is particularly well suited to data that has different noise characteristics in different dimensions, or that has non-normally distributed noise, and that therefore cannot be processed effectively using standard multidimensional peak picking algorithms. However, the invention can equally well be applied to data characterized by normally distributed noise in all dimensions.

As used herein, multidimensional data refers to data that can be understood or characterized as having multiple independent variables and a single dependent variable. The dimensionality of the data refers to the number of independent variables. For example, in the case of two-dimensional LC-MS data, the two dimensions are retention time and mass-to-charge ratio (m/z), and an ion intensity level is measured for each mass-to-charge ratio at each retention time. In this case, m/z is not a straightforward independent variable, but it can be treated as such for analysis purposes. Similar decisions can be made to apply the present invention to other data sets that are not straightforward n-dimensional data (n independent variables and one dependent variable). In fact, any data having points with at least three components, for which it is desired to select peaks in one of the components, can be analyzed using the present invention.

Peak picking (also referred to as peak detection, extraction, or selection) refers to identification of actual peaks within multidimensional data that contains noise. In data collected from an analytical instrument, peaks correspond to maxima in physical measurements containing information about the analyte. In general, peaks have a width defined by more than one data point. With respect to the measurement being made, noise has no information content. In general, noise is randomly distributed according to a measurable statistical distribution. Thus in principle, if the noise distribution is known, a suitable filter can be constructed to reduce the noise sufficiently so that peaks can be detected. In general, the peaks may be detected above the noise level provided the average intensity level of the noise is below that of the peaks.

LC-MS noise originates from a variety of sources corresponding to different components of the system. For example, chemical noise results from column bleed, i.e., long-time elution of strongly-adsorbed species at particular mass-to-charge ratios; low-concentration sample contaminants; and detection of the chromatographic mobile phase. In the mass spectrometer, the ion generation, selection, and detection processes all generate noise. Electronic signal processing and analog-to-digital conversion add white noise to the acquired data. The noise sources and distributions are not well understood for all components, making it difficult to threshold the data correctly for peak selection. In fact, as determined by the present inventor, LC-MS noise is not normally distributed, unlike, e.g., purely electrical noise. It therefore cannot be filtered effectively using standard linear filters and peak extraction algorithms. Additionally, the different noise sources can have completely different effects in the two dimensions. For example, the chromatographic mobile phase can corrupt a particular mass chromatogram (abundance versus retention time for one m/z value), making it very noisy, while the effect on the mass spectra (abundance versus m/z at one retention time) is noise only at that one mass-to-charge ratio.

Figure 3:
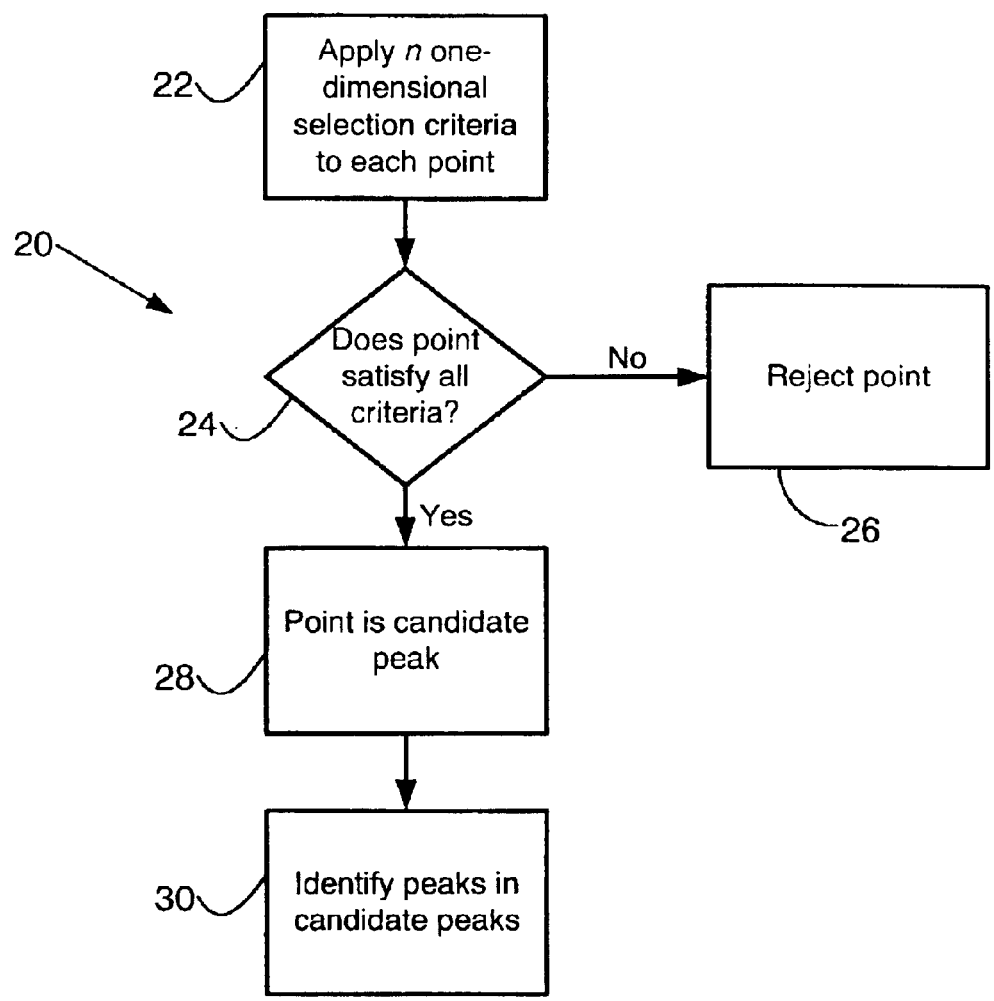
FIG. 3 is a flow diagram of a peak selection method of the present invention.

The present invention addresses this nature of LC-MS data by applying different noise thresholds to different dimensions of the data. A flow diagram of a general peak selection method 20 of the invention applied to an n-dimensional data set is shown in FIG. 3. First, in step 22, n one-dimensional peak selection criteria are applied to each data point in the data set. Preferably, a different set of n selection criteria are applied to each point. If the point does not satisfy all n one-dimensional selection criteria (step 24), then the point is rejected and not considered as a candidate peak (step 26). However, if the point satisfies all selection criteria, then it is considered to be a candidate peak (step 28), i.e., potentially, but not necessarily, an actual peak. Additional analysis is then performed in step 30 to confirm which, if any, of the candidate peaks are actual peaks. In a preferred embodiment, a clustering algorithm is applied. In the retention time dimension, peaks typically have a finite width and extend over multiple data points. Clusters of a threshold number of contiguous candidate peaks are considered to be actual peaks, while isolated candidate peaks or groups of contiguous candidate peaks containing less than the threshold number of points are rejected.

Figure 4:
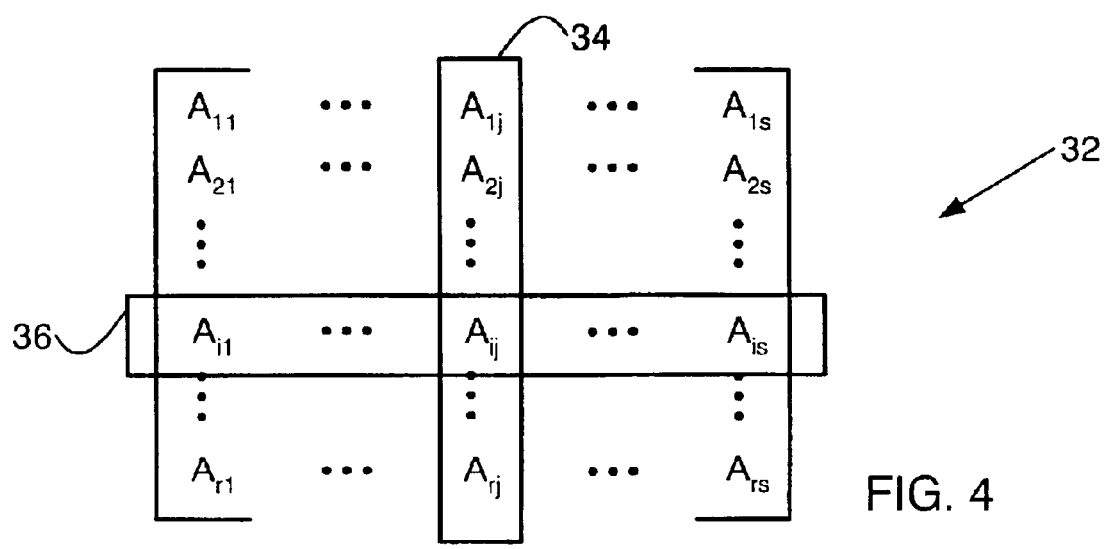
FIG. 4 is a schematic diagram of a two-dimensional data set to which one-dimensional peak selection criteria are being applied, according to the method of FIG. 3.

Application of the method to a two-dimensional data set 32 is illustrated in FIG. 4. While a two-dimensional data set is often represented on a three-dimensional plot, it is also useful to consider the data to be elements of a two-dimensional matrix $A_{ij}$ (and analogously an n-dimensional matrix for n-dimensional data), as shown. Thus, in the case of LC-MS data, each data point $A_{ij}$ is the intensity value at the $i^{th}$ discrete (e.g., integer) mass-to-charge ratio and the $j^{th}$ retention time. A single row in the matrix represents a mass chromatogram (abundance versus time for a single m/z value), while a single column represents a mass spectrum (abundance versus m/z at a single scan time). For the present invention, a row or column is considered to be a one-dimensional component of the data set; for example, $A_{i5}$ and $A_{3j}$ are vectors that are one-dimensional components of the two-dimensional matrix $A_{ij}$. Each data point is contained within n one-dimensional components of the date set. For example, the data point $A_{78}$ is contained within the two vectors $A_{7i}$ and $A_{j8}$.

As shown in FIG. 4, two one-dimensional selection criteria 34 and 36 are applied independently to the data point $A_{ij}$. That is, whether or not a data point satisfies one selection criterion is independent of its evaluation with respect to other selection criteria. In a preferred embodiment of the invention, the vertical selection criterion 34 is the same for all points within the labeled box and corresponds to the $j^{th}$ vertical component (column) of the data set. Similarly, the horizontal selection criterion 36 is the same for all points within its labeled box, i.e., corresponds to the $i^{th}$ horizontal component (row) of the data set. Each horizontal component preferably has a selection criterion that is computed separately from the criteria of all other horizontal components, and therefore likely different from other selection criteria.

The one-dimensional peak selection criteria are preferably noise thresholds, and points satisfy a criterion by exceeding the noise threshold. n noise thresholds are applied to each data point, and the point is considered to be a candidate peak only if it exceeds all n noise thresholds. The noise thresholds are computed locally, i.e., for each component vector. For example, the noise threshold of the vertical selection criterion 34 in FIG. 4 can be computed from all points within the indicated component (column), i.e., points $A_{ij}, \ldots, A_{rj}$. Alternatively, a noise threshold for a particular point can be computed from a window of points surrounding the particular point and containing fewer than r points. Using a local noise threshold is beneficial because, for LC-MS data, the noise is not uniform over the entire mass range or retention time range.

Preferably, the noise threshold is computed not from a mean value of the data points, but from a median value of the nonzero data points in the data set component. A median is preferred because it is insensitive to outliers and also relatively insensitive to the number of peaks in the subset of which the median is computed. It is therefore not affected by high-intensity peaks and accurately reflects the background noise level. In fact, any method for computing the threshold that is insensitive to outliers can be used. In a simple embodiment, the noise threshold is a multiplicative factor (e.g., between 6 and 16) of the median. Generally, a suitable multiplicative factor can be determined by trial and error and evaluated by the number and quality of resulting candidate peaks. The optimal number typically depends upon the particular application. Of course, the present invention can be implemented with any method for computing the noise threshold. A point whose value exceeds the noise threshold is considered to be a one-dimensional peak, i.e., a peak in that particular dimension.

Figure 5:
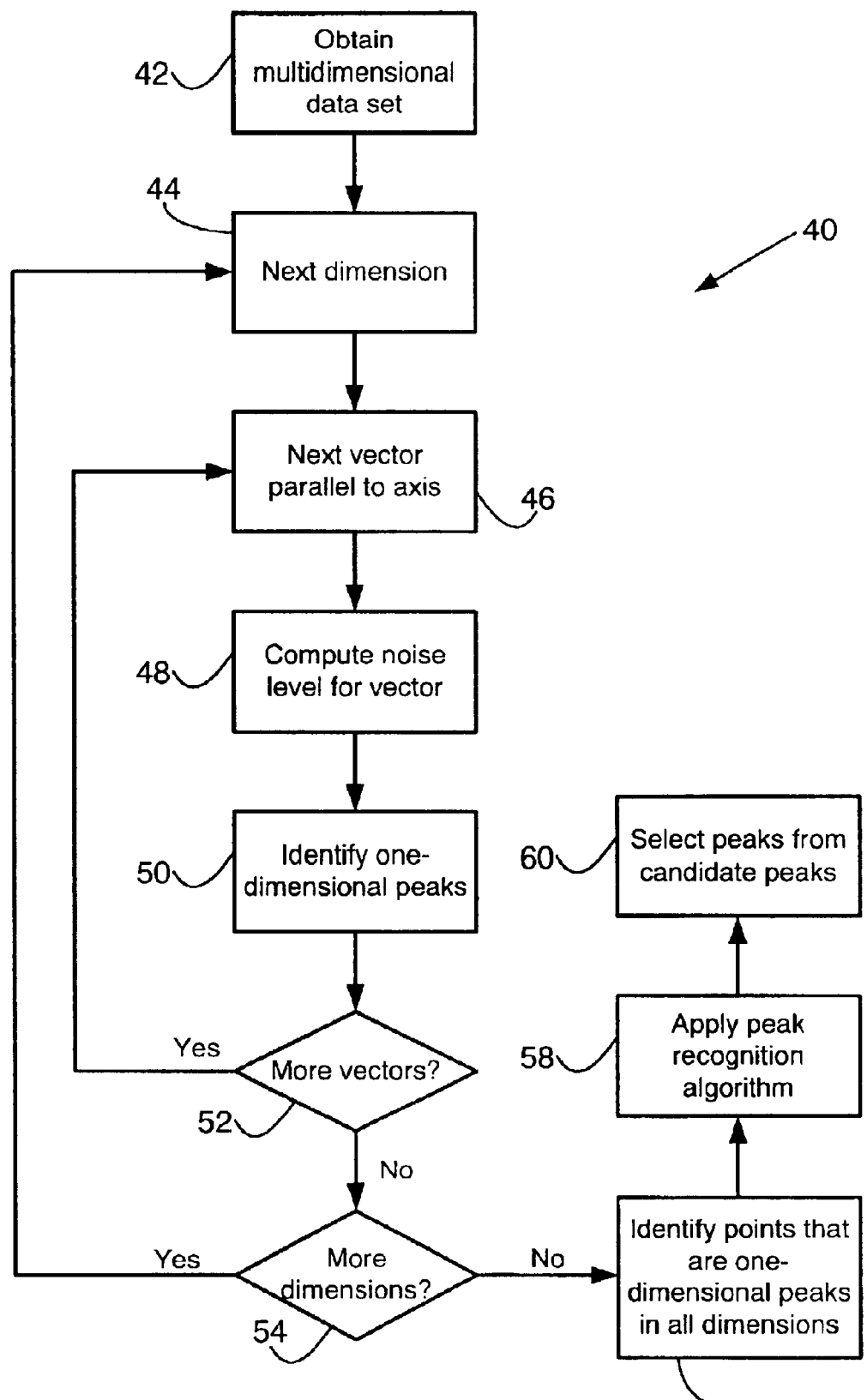
FIG. 5 is a flow diagram of a preferred embodiment of a peak selection method of the present invention.
Figure 6A:
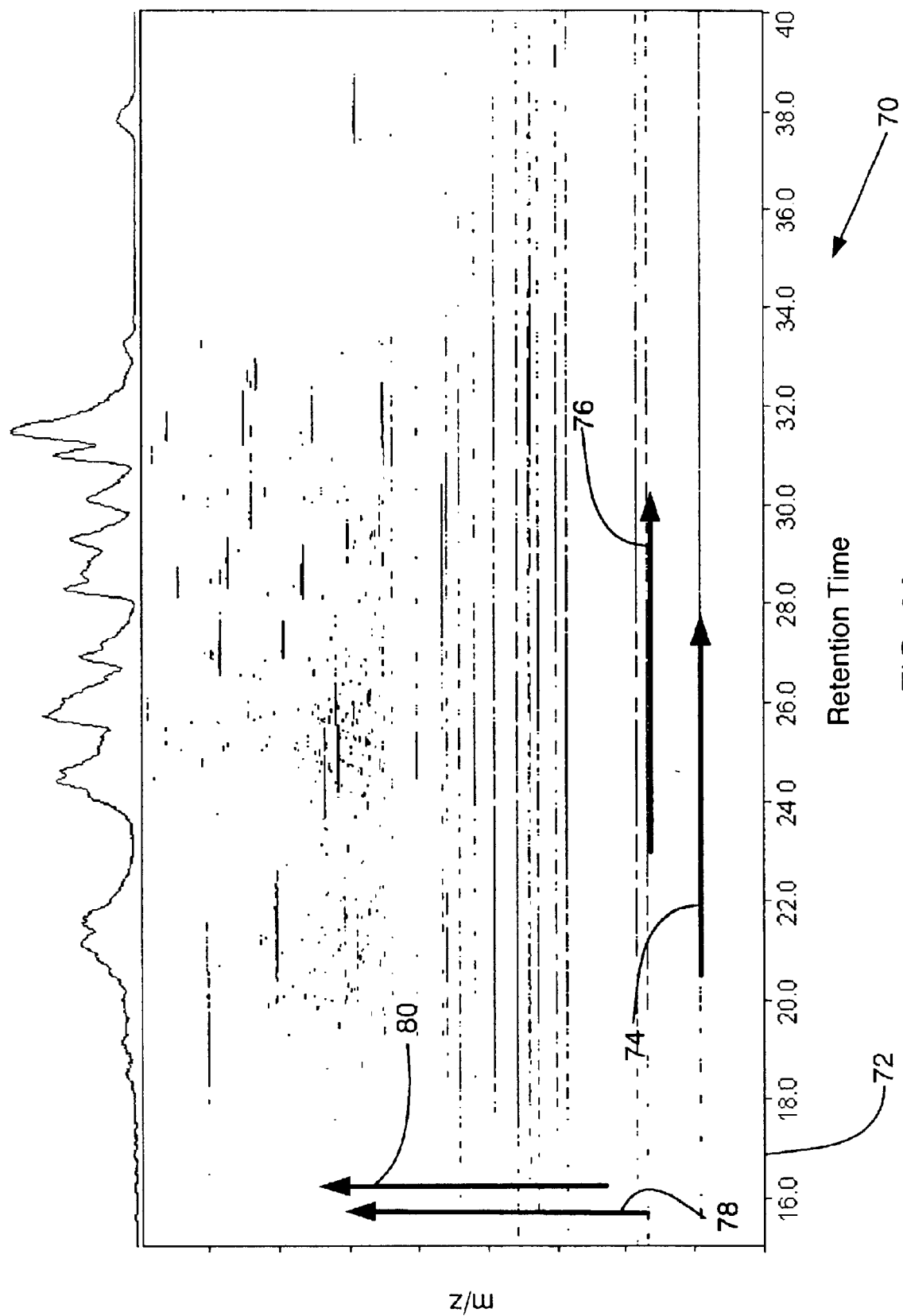
FIGS. 6A and 6B are two-dimensional LC-MS plots illustrating application of the method of FIG. 5.
Figure 6B:
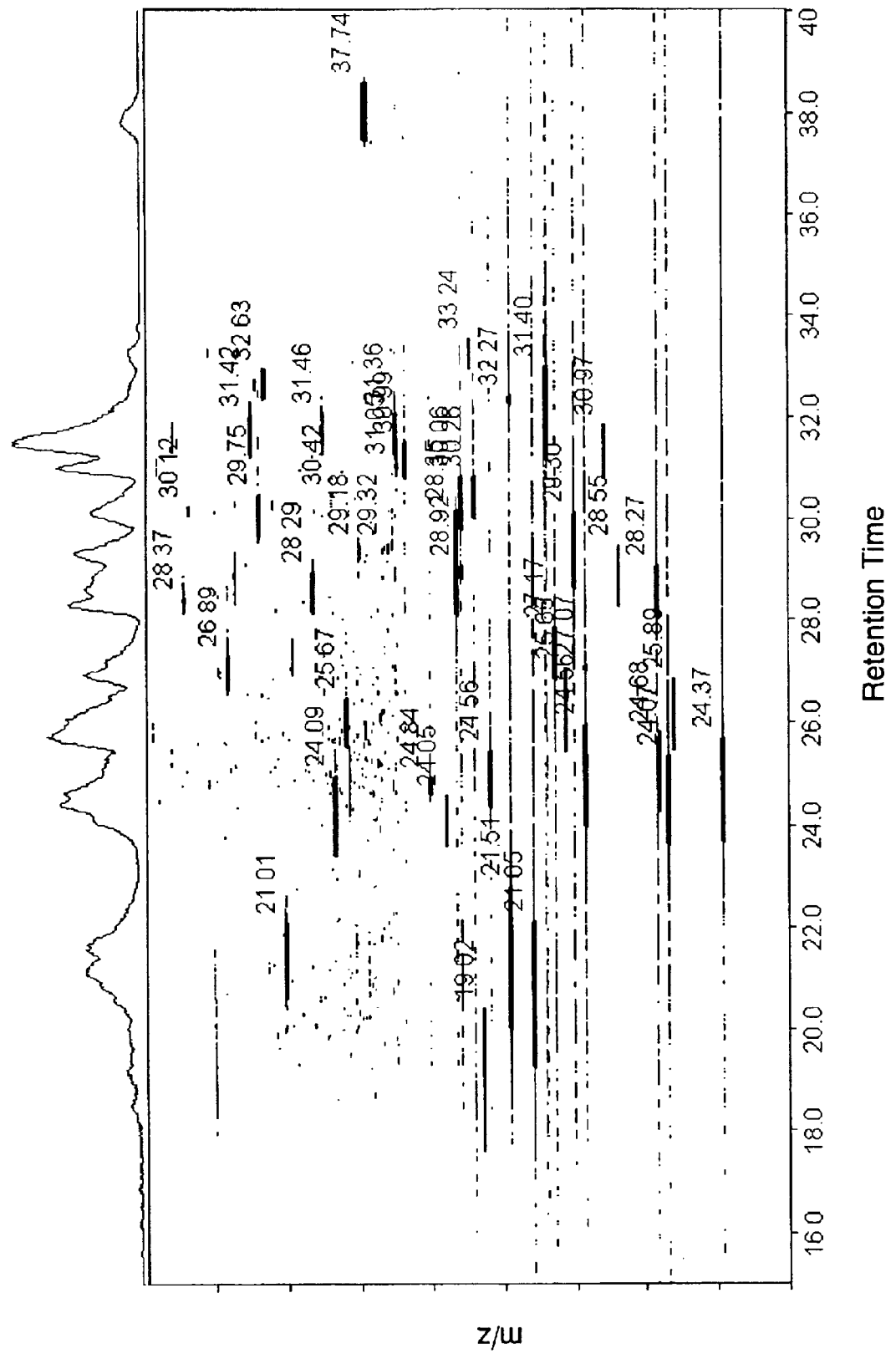

A flow diagram of a preferred embodiment of a method 40 for implementing the present invention is shown in FIG. 5. FIGS. 6A and 6B illustrate the method 40 as performed on two-dimensional intensity plots, in which the darkness of a point represents the intensity detected at that retention time and mass-to-charge ratio. The curve above the two-dimensional plot is a TIC chromatogram with a baseline correction. Each point in the TIC chromatogram is the sum of all points directly below it (i.e., at the same retention time) in the two-dimensional plot. The plots of FIGS. 6A–6B contain data obtained from a combined liquid chromatography-electrospray ionization mass spectrometry experiment on a proteolytic digest of human serum. The method 40 begins with step 42 of FIG. 5, in which a multidimensional data set (i.e., n dimensions, for n at least 2) is obtained, for example, from an analytical instrument such as a liquid chromatography-mass spectrometry instrument. In step 44, a dimension of the data (e.g., elution time or m/z) not previously examined is selected, followed by selection of a new vector parallel to the selected dimension's axis and passing through at least one data point (step 46). Selection of dimension and vector are arbitrary. For example, in the plot 70 of FIG. 6A, the horizontal axis 72, the time dimension, is first selected, and a vector 74 corresponding to the smallest value of m/z for which a data point exists is chosen. However, any vector not yet analyzed and any dimension not yet analyzed can be chosen.

Once the vector is selected, in step 48, a noise level is computed for that vector from all points through which the vector passes. In step 50, one-dimensional peaks, i.e., points on the vector whose value exceeds the computed local noise level, are identified. If the point qualifies as a one-dimensional peak, then its value is stored for future processing. Alternatively, a local noise threshold can be computed for each point on the vector from, for example, a window of points surrounding the point, to determine whether the point is a one-dimensional peak. After all data points on the vector have been examined, the system determines whether additional vectors parallel to the selected axis and passing through data points are available (step 52). If so, the method returns to step 46 to select the next vector, e.g., vector 76 of FIG. 6A. In this way, every point is considered in the sweep of one-dimensional vectors parallel to the selected axis. Note that for higher-dimensional data, the number of vectors to consider grows exponentially. For example, an additional dimension of data out of the page of FIG. 6A would require the entire plane of vectors to be considered for every value of the dimension out of the plane.

Once all vectors for a given dimension have been examined, the method determines, in step 54, whether additional unanalyzed dimensions exist. If so, the method returns to step 44 to select vectors parallel to the new axis. As shown in FIG. 6A, vector 78 is first selected, followed by vector 80 and all subsequent vectors. Again, every point in the data set is considered for the new dimension. When all dimensions have been examined, the method moves to step 56, at which time each point has been considered for selection as a one-dimensional peak n times. Thus each point can have been identified as a one-dimensional peak between zero and n times. In step 56, points are identified that were selected as one-dimensional peaks in all n dimensions. These points are termed candidate peaks because they are potentially, but not necessarily, actual peaks.

A peak recognition algorithm is applied to the candidate peaks in step 58 to select actual peaks from the candidate peaks in step 60. For example, in a preferred embodiment, contiguous candidate peaks are clustered, and a minimum number of clustered candidate peaks is considered to be a peak. A variety of clustering algorithms are known in the art; one suitable example is a recursive grassfire algorithm. Alternatively, more sophisticated peak recognition methods such as lineshape analysis or Bayesian/Maximum Likelihood analysis (for mass chromatograms) or isotope distribution analysis (for mass spectra) can be applied before, after, or during clustering. These methods are well-known in the art and will not be discussed herein. FIG. 6B illustrates the data set after candidate peaks have been clustered into peaks. A comparison between the collected data of FIG. 6A and the analyzed data of FIG. 6B reveals the dramatic reduction in data performed by the present invention. As shown, not only does the method extract peaks automatically and therefore eliminate the necessity for an operator to select peaks manually, it also dramatically reduces the amount of data required to be stored, in this case from about 30 MB to less than 10 kB. In addition, note the multiple overlapping peaks near a retention time of 32 minutes; these peaks could not have been detected with a one-dimensional peak selection algorithm.

Note that even though the data set may be acquired as (n+1)-dimensional points, it can easily be structured into an n-dimensional matrix to which the present invention is applied. Components lacking values for particular independent variables can simply be considered to have zero values at those independent variables.

In alternative embodiments of the invention, for data sets in which n>2, a point can qualify as a candidate peak even if it does not satisfy all n one-dimensional peak selection criteria. In fact, the invention includes methods in which candidate peaks satisfy two or more one-dimensional selection criteria. The number of dimensions in which the point must be a peak can be predetermined by the user and incorporated into the method. In these embodiments, m selection criteria are applied to each point, where $2 \leq m \leq n$, and candidate peaks satisfy p one-dimensional selection criteria, where $2 \leq p \leq m$. Note that each candidate peak is not required to satisfy criteria corresponding to the same dimension. For example, in a seven-dimensional data set, each candidate point can be required to satisfy conditions corresponding to the first five dimensions, in which case only these conditions need be applied to each point. Alternatively, a candidate peak can be required to satisfy any five of seven applied criteria. Any combination of values of m and p as defined above is within the scope of the invention. An application of the alternative embodiments is the combined use of three analytical techniques, e.g., LC, MS, and NMR spectroscopy. In that case, candidate peaks may be tested and qualify as one-dimensional peaks in the LC and MS dimensions only.

As with most peak selection methods, higher resolution is beneficial for clustering or post-clustering filtering of identified peaks. Higher resolution scans provide more data points for each true peak, making the peak easier to identify. With high enough resolution in the mass spectra, additional criteria can be applied. For example, isotope analysis examines m, m+1, and m+2 peaks to compare their distribution to a known isotope distribution. If the peaks have the expected distribution, then they can be selected with more confidence.

The above methods can be modified in many ways without departing from the scope of the invention. For example, a baseline correction can be applied to the data before the peak picking method is applied. The baseline correction can, for example, compensate for the low-frequency upward drift in the chromatogram over time as the mobile phase concentration changes, thereby affecting the ionization efficiency in the mass spectrometer. The data can also be smoothed, filtered, or centroided before the method is applied. Centroided data replaces the entire lineshape of a peak with a point at the average value of the independent variables in multidimensional space. In fact, data obtained from a mass spectrometer is often not raw data, but has already been centroided or otherwise modified before made available to the user.

The methods of the invention can also be used as one step of a peak selection process. For example, after peaks have been selected from the candidate peaks using the present invention, additional criteria can be applied to the peaks before they are accepted and stored in a peak database. Alternatively, the method of the invention can be applied after an initial peak finding algorithm has been applied. In this case, the method of the invention confirms that the selected peaks satisfy a peak selection criterion in all dimensions.

Note that although the method has been described for LC-MS data, it can be applied to any multidimensional data in which peaks are detected. In particular, data collected by other chromatographies (e.g., gas), spectroscopies, or capillary electrophoresis would benefit from methods of the invention. For example, LC-NMR is a hyphenated method combining chromatography with nuclear magnetic resonance spectroscopy. LC-LC-MS methods add an additional chromatography dimension and are well suited for analysis by the present invention.

Figure 7:
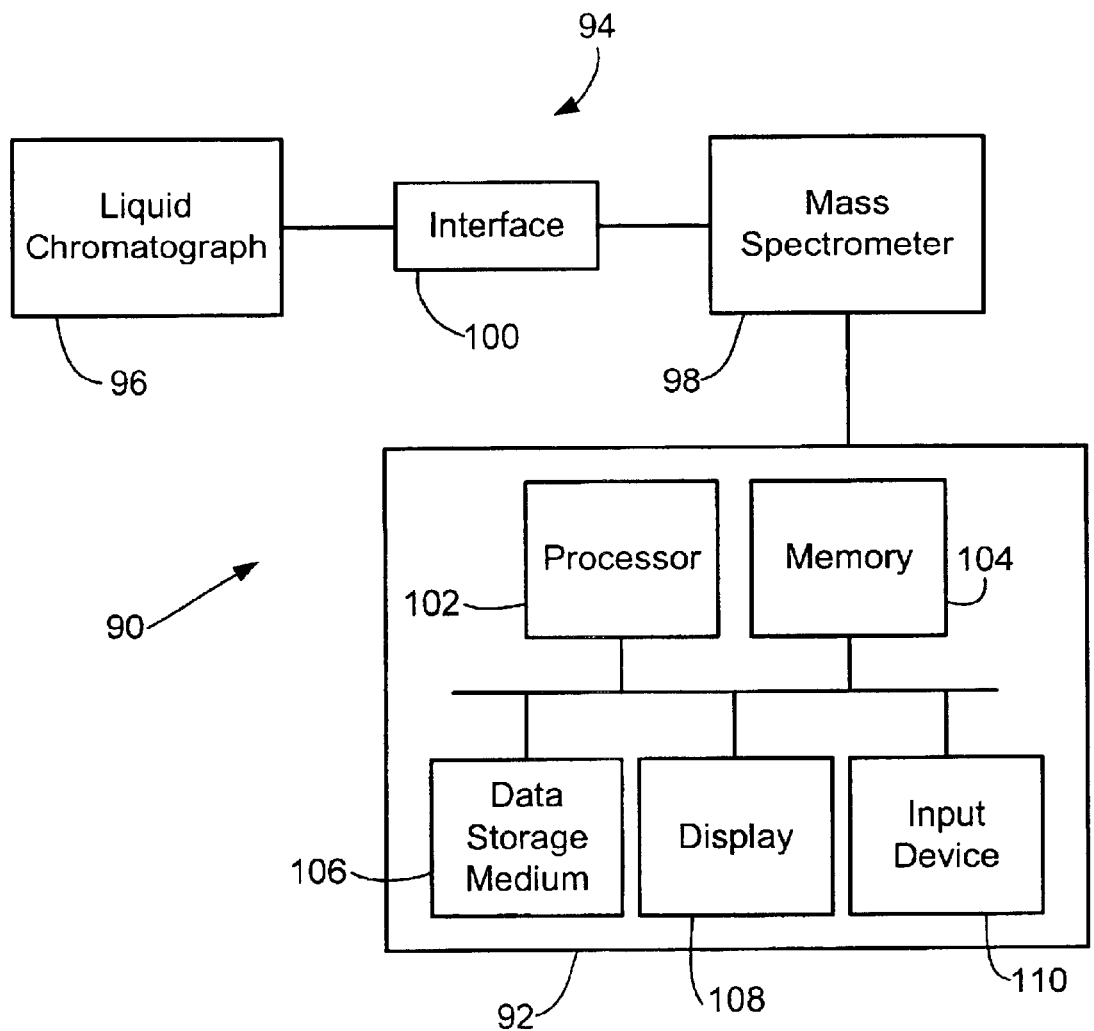
FIG. 7 is a block diagram of a hardware system for implementing methods of the invention.

Although not limited to any particular hardware configuration, the present invention is typically implemented in software by a system 90, shown in FIG. 7, containing a computer 92 in communication with an analytical instrument, in this case a LC-MS instrument 94 that includes a liquid chromatography instrument 96 connected to a mass spectrometer 98 by an interface 100. The computer 92 acquires raw data directly from the instrument 94 via an analog-to-digital converter. Alternatively, the invention can be implemented by a computer in communication with an instrument computer that obtains the raw data. Of course, specific implementation details depend on the format of data supplied by the instrument computer. Preferably, the entire process is automated: the user sets the instrument parameters and injects a sample, the two-dimensional data are acquired, and peaks are selected for transfer to a suitable database.

The computer 92 implementing the invention typically contains a processor 102, memory 104, data storage medium 106, display 108, and input device 110. Methods of the invention are executed by the processor 102 under the direction of computer program code stored in the computer 92. Using techniques well known in the computer arts, such code is tangibly embodied within a computer program storage device accessible by the processor 102, e.g., within system memory 104 or on a computer readable storage medium 106 such as a hard disk or CD-ROM. The methods may be implemented by any means known in the art. For example, any number of computer programming languages, such as Java, C++, or LISP may be used. Furthermore, various programming approaches such as procedural or object oriented may be employed.

It is to be understood that the steps described above are highly simplified versions of the actual processing performed by the computer 92, and that methods containing additional steps or rearrangement of the steps described are within the scope of the present invention.

It should be noted that the foregoing description is only illustrative of the invention. Various alternatives and modifications can be devised by those skilled in the art without departing from the invention. Accordingly, the present invention is intended to embrace all such alternatives, modifications and variances which fall within the scope of the disclosed invention.

What is claimed is:

1. A method for automatically detecting peaks in an n-dimensional data set, where $n \geq 2$, comprising:

acquiring said n-dimensional data set from an analytical instrument;

independently applying m one-dimensional peak selection criteria to each data point in said data set, wherein $2 \leq m \leq n$, each peak selection criterion corresponding to a particular dimension; and identifying candidate peaks in said data points, wherein each candidate peak satisfies p of said m applied selection criteria, wherein $2 \leq p \leq m$.

2. The method of claim 1, wherein m=n.

3. The method of claim 2, wherein p=n.

4. The method of claim 1, wherein one-dimensional selection criteria corresponding to the same dimension and applied to different data points are not necessarily identical.

5. The method of claim 1, wherein one-dimensional selection criterion applied to a particular data point is computed from a one-dimensional component of said data set that includes said particular data point.

6. The method of claim 1, wherein each selection criterion comprises a threshold value.

7. The method of claim 6, wherein said threshold value is computed from a subset of said data points.

8. The method of claim 7, wherein said threshold value is computed from a median of said subset of said data points.

9. The method of claim 1, further comprising identifying peaks in said candidate peaks using a peak recognition algorithm.

10. The method of claim 9, wherein said peak recognition algorithm comprises clustering said candidate peaks.

11. The method of claim 9, wherein said peak recognition algorithm comprises an algorithm selected from the group consisting of lineshape analysis, Bayesian analysis, maximum likelihood analysis, and isotope distribution analysis.

12. The method of claim 1, wherein said n-dimensional data set comprises two-dimensional chromatography-spectrometry data.

13. The method of claim 12, wherein said n-dimensional data set comprises liquid chromatography-mass spectrometry data, and wherein said peaks represent ionized components of a chemical mixture.

14. A method for detecting components in a chemical mixture, comprising:

subjecting said mixture to chromatography and mass spectrometry using an instrument;

acquiring a two-dimensional data set comprising mass spectra and mass chromatograms from said instrument;

computing a local noise threshold for each acquired mass spectrum and for each acquired mass chromatogram;

applying corresponding mass spectrum and mass chromatogram noise thresholds to each data point in said two-dimensional data set; and identifying candidate peaks, wherein each candidate peak exceeds said corresponding mass spectrum noise threshold and said corresponding mass chromatogram noise threshold.

15. The method of claim 14, wherein said local noise threshold for said acquired mass spectrum is computed from a median of nonzero points in said mass spectrum.

16. The method of claim 14, wherein said local noise threshold for said acquired mass chromatogram is computed from a median of nonzero points in said mass chromatogram.

17. A program storage device accessible by a processor, tangibly embodying a program of instructions executable by said processor to perform method steps for automatically detecting peaks in an n-dimensional data set, where $n \geq 2$, said method steps comprising:

acquiring said n-dimensional data set from an analytical instrument;

independently applying m one-dimensional peak selection criteria to each data point in said data set, wherein $2 \leq m \leq n$, each peak selection criterion corresponding to a particular dimension; and identifying candidate peaks in said data points, wherein each candidate peak satisfies p of said m applied selection criteria, wherein $2 \leq p \leq m$.

* * * * *